(12) United States Patent
Teoh et al.

(10) Patent No.: US 6,730,252 B1
(45) Date of Patent: May 4, 2004

(54) METHODS FOR FABRICATING A FILAMENT FOR USE IN TISSUE ENGINEERING

(76) Inventors: Swee Hin Teoh, 22 Toh Yi Road, Singapore 596504 (SG); Dietmar Werner Hutmacher, Upper Bukit Timah Road, 48 Toh Tuck Road, Signature Park #03-07, Singapore (SG); Kim Cheng Tan, Blk 856D, Tampines St. 82, #12-180, Singapore 524856 (SG); Kock Fye Tam, Blk 659, Woodland Ring Road, #02-174, Singapore 730659 (SG); Iwan Zein, Blk 7, Siglap Road, #18-72 Mandarin Gardens, Singapore 448909 (SG)

( * ) Notice: Subject to any disclaimer, the term of this patent is extended or adjusted under 35 U.S.C. 154(b) by 0 days.

(21) Appl. No.: 09/957,407

(22) Filed: Sep. 20, 2001

Related U.S. Application Data

(60) Provisional application No. 60/233,874, filed on Sep. 20, 2000.

(51) Int. Cl.[7] .............................. D01D 5/088; D01F 6/60
(52) U.S. Cl. .............................. 264/178 F; 264/211.14; 264/234
(58) Field of Search .................. 264/178 F, 211.14, 264/234

(56) References Cited

U.S. PATENT DOCUMENTS 5,294,395 A * 3/1994 Broyer ................ 264/178 F

OTHER PUBLICATIONS

Zein, Iwan et al., "Fused deposition modeling of novel scaffold architectures for tissue engineering applications", Biomaterials 23 (2002), pp. 1169–1185.

* cited by examiner

Primary Examiner—Leo B. Tentoni
(74) Attorney, Agent, or Firm—Pandiscio & Pandiscio, P.C.

(57) ABSTRACT

The invention relates to the use of Fused Deposition Modeling to construct three-dimensional (3D) bioresorbable scaffolds from bioresorbable polymers such as polycaprolactone (PCL), or from composites of bioresorbable polymers and ceramics, such as polycaprolactone/hydroxyapatite (PCL/HA). Incorporation of a bioresorbable ceramic to produce a hybrid/composite material support provides the desired degradation and resorption kinetics. Such a composite material improves the biocompatibility and hard tissue integration and allows for increased initial flash spread of serum proteins. The basic resorption products of the composite also avoids the formation of an unfavorable environment for hard tissue cells due to a decreased pH. The scaffolds have applications in tissue engineering, e.g., in tissue engineering bone and cartilage.

39 Claims, 7 Drawing Sheets

(a) (b)

(a)          (b)

(a) (b) (c)

METHODS FOR FABRICATING A FILAMENT FOR USE IN TISSUE ENGINEERING

REFERENCE TO PENDING PRIOR PATENT APPLICATION

This patent application claims benefit of pending prior U.S. Provisional Patent Application Ser. No. 60/233,874, filed Sep. 20, 2000 by Swee Hin Teoh et al. for THREE-DIMENSIONAL BIORESORBABLE SCAFFOLDS FOR TISSUE ENGINEERING APPLICATIONS, which patent application is hereby incorporated herein by reference.

FIELD OF THE INVENTION

This invention relates to medical apparatus and methods in general, and more particularly to apparatus and methods for tissue engineering.

BACKGROUND OF THE INVENTION

Tissue engineering is a truly multidisciplinary field, which applies the principles of engineering, life science, and basic science to the development of viable substitutes that restore, maintain, or improve the function of human tissues. Large-scale culturing of human or animal cells (including but not limited to skin, muscle, cartilage, bone, marrow, endothelial and stem cells) may provide substitutes to replace damaged components in humans. Naturally derived or synthetic materials are fashioned into "scaffolds" that, when implanted in the body as temporary structures, provide a template that allows the body's own cells to grow and form new tissues while the scaffold is gradually absorbed. Conventional two-dimensional scaffolds are satisfactory for multiplying cells, but are less satisfactory when it comes to generating functional tissues. For that reason, a three-dimensional (3D) bioresorbable scaffold system is preferred for the generation and maintenance of highly differentiated, tissues. Ideally, the scaffold should have the following characteristics: (i) be highly porous with an interconnected pore network for cell growth and flow transport of nutrients and metabolic waste; (ii) be biocompatible and bioresorbable, with controllable degradation and resorption rates so as to substantially match tissue replacement; (iii) have suitable surface chemistry for cell attachment, proliferation and differentiation; and (iv) have mechanical properties to match those of the tissues at the site of implantation. In vivo, the scaffold structure should protect the inside of the pore network proliferating cells and their extracellular matrix from being mechanically over-loaded for a sufficient period of time. This is particularly important for load-bearing tissues such as bone and cartilage.

Bone Tissue Engineering

It is estimated that the number of bone repair procedures performed in the United States alone is over 800,000 per year. Today, skeletal reconstruction has become an increasingly common and important procedure for the orthopedic surgeon. The traditional biological methods of bone-defect management include autografting and allografting cancellous bone, applying vascularized grafts of the fibula and iliac crest, and using other bone transport techniques. Today, bone grafting is increasing and the failure rate is unacceptably high. In patients who receive various bone grafts, a failure rate ranging from 16% to 50% is reported. The failure rate of autografts is at the lower end of this range, but the need for a second (i.e., donor) site of surgery, limited supply, inadequate size and shape, and the morbidity associated with the donor site are all major concerns. Furthermore, the new bone volume maintenance can be problematic due to unpredictable bone resorption. In large defects, the body can resorb the grafts before osteogenesis is complete. Furthermore, not only is the operating time required for harvesting autografts expensive, but often the donor tissue is scarce, and there can be significant donor site morbidity associated with infection, pain, and hematoma. Allografting introduces the risk of disease and/or infection; it may cause a lessening or complete loss of the bone inductive factors. Vascularized grafts require a major microsurgical operative procedure requiring a sophisticated infrastructure. Distraction osteogenesis techniques are often laborious and lengthy processes that are reserved for the most motivated patients.

Engineering osseous tissue by using cells in combination with a synthetic extracellular matrix is a new approach compared to the transplantation of harvested tissues. Numerous tissue-engineering concepts have been proposed to address the need for new bone graft substitutes. One potentially successful repair solution seeks to mimic the success of autografts by removing cells from the patient by biopsy and then growing sufficient quantities of mineralized tissue in vitro on implantable, 3D scaffolds for use as functionally equivalent autogenous bone tissue. In this way, reproducing the intrinsic properties of autogenous bone material creates an ideal bony regeneration environment, which includes the following characteristics: (i) a highly porous, 3D architecture allowing osteoblast, osteoprogenitor cell migration and graft revascularization; (ii) the ability to be incorporated into the surrounding host bone and to continue the normal bone remodeling processes; and (iii) the delivery of bone-forming cells and osteogenic growth factors to accelerate healing and differentiation of local osteoprogenitor cells.

Cartilage Tissue Engineering

Research on cartilage goes back more than 250 years when Hunter stated in 1743, "From Hippocrates to the present age, it is universally known that ulcerated cartilage is a troublesome thing and that once destroyed, is not repaired". Since then, a substantial amount of research has been conducted on hyaline cartilage, fibrocartilage and elastic cartilage, with significant advances in our understanding of the development biology and biological cartilage repair process being made over the past four decades. However, the cartilage repair and regeneration response is limited in terms of form and function. While many surgical techniques and drug treatments have been proposed over the past 10 years, none have successfully regenerated long-lasting cartilage tissue to replace damaged or diseased cartilage from a clinical point of view. In fact, most of the surgical interventions to repair damaged cartilage have been directed toward the treatment of clinical symptoms rather than the regeneration of hyaline cartilage, such as pain relief and functional restoration of joint structures and articulating surfaces.

Since cartilage is limited in its ability to repair, significant efforts have also been dedicated to growing cartilage ex vivo or to supplement implants with cells to improve healing. Modern tissue engineering approaches, such as the transplantation of isolated and seeded chondrocytes in combination with bioresorbable polymeric scaffolds of synthetic and natural origin, have recently demonstrated significant clinical potential for the regeneration of different cartilaginous tissues. The success of chondrocyte transplantation and/or the quality of neocartilage formation strongly depends on the specific cellcarrier material.

Current research has largely focused on chondrocyte interaction with biodegradable polymers and devices that are FDA approved, namely, foams and textiles made of poly (glycolic acid) (PGA), poly (L-lactic acid). (PLLA) and their copolymer, poly (DL-lactic-co- glycolic acid) (PLGA). The physical and mechanical scaffold properties can have a profound effect on the healing response of the cartilage. Furthermore, the proper mechanical environment of chondrocytes and their matrix is essential to obtain a structurally and biochemically functional tissue. PGA and PLA and their copolymers have frequently been chosen for tissue engineering applications because their degradation can be tailored. In a highly porous configuration, however, their mechanical properties may be limited.

Bone Grafting in Craniofacial Surgery

The clinical goals for craniofacial skeletal reconstruction are multifaceted. Aesthetic and functional considerations often dictate the use of malleable implant materials. However, in most cases these three-dimensional shaped implants must also provide immediate structural integrity. The host-graft interface should not produce an immunological or inflammatory response to minimize peri-implant morbidity.

Successful craniofacial surgical experience with the patient's own bone has made it the graft material against which all others are measured. Unfortunately, autografted bone is limited in amount and desired morphology. In addition, the use of the patient's own bone is associated with donor-site morbidity and graft resorption. When autogenous tissue is not available, or its use is limited because of defect size or shape, a variety of alloplastic materials are used for craniofacial reconstruction. Metallic, ceramic, and synthetic polymer materials are readily available. However, all metals, most ceramics, and many polymers are not designed to degrade and resorb, and the potential for replacement by host tissue does not exist. Furthermore, if the soft tissues surrounding an alloplastic material implant site were previously more firmly attached to an underlying bony surface, they may now move relative to the implanted alloplastic material. These undesirable mechanical interactions can result in seroma formation and soft tissue inflammation. Clinically, foreign body reactions are observed and long-term problems include a minimal potential for new bone growth and poor remodeling adjacent to the reconstructed area.

Stress shielding of nearby bone from the alloplastic transplant, due to the mismatch of the mechanical properties of the synthetic implant and host bone, can lead to local tissue atrophy and necrosis. Currently, polymethylmethacrylate (PMMA) is probably the most commonly used alloplastic material for reconstruction of significant craniofacial, defects. Often referred to as bone cement, PMMA is used on a routine basis as an alternative to bone autografts in reconstructing cranial defects because: (1) it can withstand the mechanical forces of the craniofacial skeleton, thus providing support and protection to underlying soft tissue structures; (2) it is an inexpensive implant material when compared to an autograft; and (3) it demonstrates sufficient biocompatibility with adjacent soft tissues.

Although primary tissue reaction of PMMA has been rarely observed, secondary foreign body reactions have been reported. Hence, the threshold for indirect infection at the surgical site is lowered. In general, PMMA is used to fill bony defects by one of two methods: it can be polymerized in situ or it can be molded and placed into the defect. Due to in vivo polymerization of PMMA, a significant exothermic reaction takes place with temperatures reaching 81° C. The reaction can result in thermal injury to, and necrosis of, adjacent host bone, dura, and other soft tissues.

Rapid Prototyping

Many different processing techniques have been developed to design and fabricate three-dimensional (3D) scaffolds for tissue engineered implants. These conventional techniques include fiber bonding, solvent casting, particulate leaching, membrane lamination, melt molding, temperature-induced phase separation (TIPS), and gas foaming. A wide range of scaffold characteristics, such as porosity and pore size, has been reported using such fabrication techniques. However, there are numerous drawbacks to using such scaffolds for tissue engineering applications. For one thing, the pores are not fully interconnected due to the formation of skin-layers during solvent evaporation. And the pore size varies, as it is difficult to ensure that the porogens are well-dispersed and not agglomerated to form bigger particles. In addition, the thickness and length of the pore walls and edges vary, depending on the solvent evaporation rate. Also, the scaffolds cannot be made with thick sections inasmuch as deeply embedded porogens become too distant from the surface and residual porogens may be left in the final structure. And the use of organic solvents requires careful and complete removal of residual solvents prior to clinical usage. In addition, the aforementioned conventional scaffold fabrication techniques do not allow the fabrication of a 3-D scaffold with a varying multiple layer design. Such matrix architecture is advantageous in instances where be tissue engineers want to grow a bi- or multiple tissue interface, e.g., an articular cartilage/bone transplant. Rapid Prototyping machines (RP), such as Fused Deposition Modelling (FDM) and 3D Printing (3DP) which build a physical model by depositing layers of a material one at a time, allow such a design.

Rapid Prototyping (RP) is a technology that produces models and prototype parts from 3D computer-aided design (CAD) model data and model data created from 3D object digitizing systems. Unlike milling machines, which are subtractive in nature, RP systems join together liquid, powder and sheet materials to form parts. Layer by layer, REP machines fabricate plastic, wood, ceramic and metal objects using thin horizontal cross sections directly from a computer generated model. Rapid prototyping technologies allow the development of manufacturing approaches to create porous scaffolds that mimic the microstructure of living materials.

The application of rapid prototyping (RP) technologies in medicine has, until recently, been largely restricted to the surgical planning and simulation for reconstructive surgery, e.g., to the fabrication of prosthesis models such as cranial titanium plates to repair skull defects.

3DP has been used to process bioresorbable scaffolds for tissue engineering applications. The technology is based on the printing of a binder through a print head nozzle onto a powder bed. However, the removal of entrapped powder is typically quite difficult. The entire 3DP process is performed under room temperature conditions whereas FDM uses a thermoplastic polymer. Hence 3DP allows the incorporation of biological agents, such as cells, growth factors, and so forth, without inactivation if non-toxic binders such as water can be used. Unfortunately, aliphatic polyesters can generally only be dissolved in highly toxic solvents such as chloroform and methylene chloride. To date, only bioresorbable scaffolds without biological agents within the polymer matrix and in combination with particle leaching have been processed by 3DP. In addition, the mechanical properties and accuracy of the specimens manufactured by 3DP still have to be significantly improved.

Other RP technologies, such as stereolithography (SLA) and Selective Laser Sintering (SLS), pose significant material (non-bioresorbable) constraints for the manufacture of tissue engineering scaffolds. Ballistic Particular Manufacturing (BPM) is also limited by the lack of suitable biodegradable materials. Metal and metal composites have been proposed as processing materials for BPM.

Fused Deposition Modelling

Fused Deposition Modelling (FDM) is an additive manufacturing process that forms 3D objects through the extrusion and deposition of individual layers of thermoplastic materials. It begins with the creation of a conceptual CAD model on the computer. The model is imported into software (e.g., the QuickSlice™ software offered by Stratasys Inc. of Eden Prairie, Minn.) which mathematically slices the conceptual model into horizontal layers. This is followed by the creation of deposition paths within each sliced layer. The tool path data is then downloaded to the FDM machine for scaffold fabrication. A software package (e.g., SupportWorks offered by Straftasys Inc.) automatically generates supports if needed. The FDM system operates in the X, Y and Z axes. In effect, it draws the designed model one layer at a time. The FDM method involves the melt extrusion of filament materials through a heated nozzle and deposition as thin solid layers on a platform. The nozzle is positioned on the surface of a build platform at the start of fabrication. It is part of the extruder head (FDM head), which also encloses a liquefier to melt the filament material fed through two counter-rotating rollers. Each layer is made of "raster roads-"deposited in the x and y directions. A "fill gap" can be programmed between the roads to provide horizontal channels. Subsequent layers are deposited with the x-y direction of deposition—the "raster angle" programmed to provide different lay-down patterns.

Thermoplastic polymer material feeds into the temperature-controlled FDM extrusion head, where it is heated to a semi-liquid state. The head extrudes and deposits the material in ultra-thin layers onto a fixtureless base. The head directs the material into place with precision. The material solidifies, laminating to the preceding layer. Parts are fabricated in layers, where each layer is built by extruding a small bead of material, or road, in a particular lay-down pattern, such that the layer is covered with the adjacent roads. After a layer is completed, the height of the extrusion head is increased and the subsequent layers are built to construct the part. Usually, FDM is used to fabricate solid models. For the purpose of fabricating porous structures, a positive value is applied to the raster fill gap to impart a channel within a build layer. Arranged in a regular manner, the channels are interconnected even in three dimensions. The layer by layer fabrication allows design of a pore morphology which varies across the scaffold structure. At present, only a few non-resorbable polymeric materials, such as polyamide, ABS, resins, etc. are used in the FDM RP systems.

Poly(caprolactone) (PCL) is a semicrystalline, bioresorbable polymer belonging to the aliphatic polyester family. It has favorable properties for thermoplastic processing. It has a low glass transition temperature ($T_g$) of −60° C., a melting point ($T_m$) of 60° C. and a high decomposition temperature of 350° C., with a wide range of temperatures which allow extrusion. At present, PCL is regarded as a soft and hard tissue-compatible bioresorbable material.

The present invention uses FDM to process a bioresorbable polymer, polycaprolactone (PCL), as well as a bioresorbable composite of two biomaterials, synthetic polymer (PCL) and ceramic, to meet all the criteria for use in tissue engineering applications.

SUMMARY OF THE INVENTION

The present invention relates to the use of FDM to construct three-dimensional (3D) bioresorbable scaffolds from polycaprolactone (PCL), and from composites of PCL and ceramics, such as tricalcium phosphate (TCP) and hydroxyapatite (HA), with specific lay-down patterns that confer the requisite properties for tissue engineering applications.

The 3D polymer matrix has degradation and resorption kinetics of 6 to 12 months and,the capability to maintain a given space under biomechanical stress/loading for 6 months. Incorporation of a bioresorbable ceramic in the bioresorbable, synthetic and natural polymer produces a hybrid/composite material support triggering the desired degradation and resorption kinetics. Such a composite material improves the biocbmpatibility and hard tissue integration: the HA/TCP particles, which are embedded into the synthetic polymer matrix, allow for increased initial flash spread of serum proteins compared to the more hydrophobic polymer surface. Furthermore, the basic resorption products of the HA/TCP help buffer the acidic resorption by-products of the aliphatic polyester and thereby help to avoid the formation of an unfavorable environment for the hard tissue cells due to a decreased pH.

The resulting scaffolds have applications in tissue engineering such as tissue engineering bone and cartilage.

In one form of the invention, there is provided a method for fabricating a filament for use in tissue engineering, the method comprising:

providing a polycaprolactone material;

melting the polycaprolactone material at a first given temperature to form a polycaprolactone melt;

holding the temperature of the polycaprolactone melt at the first given temperature for a given amount of time;

lowering the temperature of the polycaprolactone melt from the first given temperature to a second given temperature after the step of holding the temperature of the polycaprolactone melt at the first given temperature for the given amount of time;

extruding the polycaprolactone melt through a fiber-spinning machine, the fiber-spinning machine having spinnerets with a die exit of a given diameter, a piston set at a given speed, and a vertical drop of a given distance from the die exit to a cooling material positioned below the die exit, wherein the combination of the second given temperature, the given die exit diameter, the given piston speed, and the given distance of the vertical drop produces the filament with a given diameter for use in tissue engineering.

In another form of the invention, there is provided a method for fabricating a filament for use in tissue engineering, the method of fabricating the filament comprising:

providing polycaprolactone pellets;

melting the polycaprolactone pellets at about 190° C. to form a polycaprolactone melt;

holding the temperature of the polycaprolactone melt at about 190° C. for about 15 minutes;

lowering the temperature of the polycaprolactone melt from the first given temperature to about 140° C. after the step of holding the temperature of the polycaprolactone melt at about 190° C. for about 15 minutes; and extruding the polycaprolactone melt through a fiber-spinning machine, the fiber-spinning machine having spinnerets with a die exit of about 1.63 mm, a piston set at about 10 mm/min, and a vertical drop of about 40 mm from the die exit to water positioned below the die exit, wherein the combination of the lower temperature of about 140° C., the die exit diameter of about 1.63, the piston speed of about 10 mm/min, and the vertical drop of about 40 mm produces the filament with a given diameter for use in tissue engineering;

wherein the given diameter of the filament corresponds to drive wheels of an unmodified Fused Deposition Modeling (FDM) system;

wherein the filament is configured to have a constant diameter; and wherein the filament is vacuum-dried and kept in a dessicator prior to usage.

And in another form of the invention, there is provided a method for fabricating a filament for use in tissue engineering, the method comprising:

providing a polycaprolactone material drying the polycaprolactone material at a first given temperature for a first given amount of time to form a dried polycaprolactone material;

combining the dried polycaprolactone material with a HA and methylene chloride mixture to form a PCL/HA blend;

stirring the PCL/HA blend at a second given temperature for a second given amount of time to form a solvent mixture;

casting the solvent mixture on a tray at a third given temperature for a third given amount of time to evaporate the solvent mixture to form a PCL/HA composite foam material;

melting the PCL/HA composite foam material at a fourth given temperature to form a PCL/HA melt;

holding the temperature of the PCL/HA melt at the fourth given temperature for a fourth given amount of time;

lowering the temperature of the PCL/HA melt from the fourth given temperature to a fifth given temperature after the step of holding the temperature of the PCL/HA melt at the fourth given temperature for the fourth given amount of time; and extruding the PCL/HA melt through a fiber-spinning machine, the fiber spinning machine having spinnerets with a die exit of a given diameter, a piston set at a given speed, and a vertical drop of a given distance from the die exit to a cooling material positioned below the die exit, wherein the combination of the fifth given temperature, the given die exit diameter, the given piston speed, and the given distance of the vertical drop produces the filament with a given diameter for use in tissue engineering.

In another form of the invention, there is provided apparatus for use in tissue engineering, the apparatus comprising:

a scaffold structure being formed of a plurality of horizontal layers of material;

vertical walls forming each of the plurality of horizontal layers of material, the walls of each layer of the plurality of horizontal layers each having a height, each being horizontally separated from one another, and defining an orientation;

adjacent pairs of the vertical walls of each of the plurality of horizontal layers of material forming channels therebetween, the channels having a depth and a width created by the height of the walls and the horizontal separation of the adjacent pairs of the vertical walls, respectively;

adjacent layers in the plurality of horizontal layers of material being in different orientations to one another wherein the orientation defined by adjacent ones of the each layer of the walls of the plurality of horizontal layers differ from one another, the different orientations providing a group of cross-points to allow adhesion between the adjacent layers and providing interconectivity between the channels throughout the scaffold structure.

And in another form of the invention, there is provided a method for fabricating a customized scaffold structure for use in tissue engineering for an individual patient, the method comprising:

obtaining a digital scan of an anatomical component of the individual patent;

obtaining a desired zone of the digital scan of the anatomical component of the individual patent;

converting the desired zone of the digital scan of the anatomical component of the individual patent to an Fused Deposition Modeling (FDM) system compatible format;

slicing the desired zone of the digital scan of the FDM system compatible format into multiple layers so as to create a sliced model of the customized scaffold structure for fused deposition modeling;

creating tool path data for fused deposition modeling using the sliced model of the customized scaffold structure;

exporting the tool path data of the sliced model of the customized scaffold structure to a Fused Deposition Modeling (FDM) system; and creating the customized scaffold structure using the tool path data of the sliced model of the customized scaffold structure and the Fused Deposition Modeling (FDM) system.

DETAILED DESCRIPTION OF THE INVENTION

Overview

Figure 1:
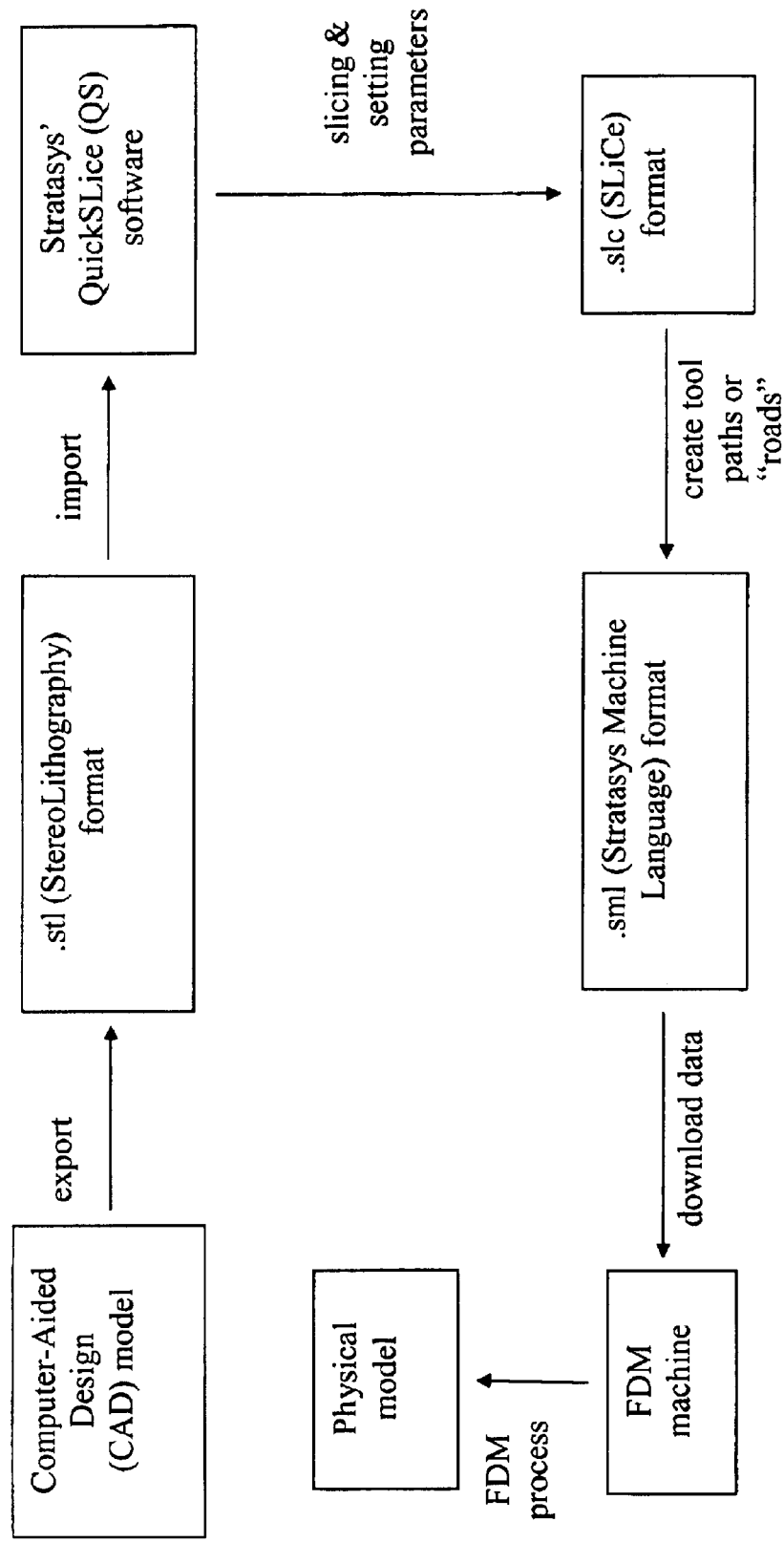
FIG. 1 represents a flow chart of the data preparation for the FDM process.

The unique ability of RP technologies to provide a customized article to suit individual patient's needs leads to the possibility of using the same for medical use, especially tissue engineering. To create the scaffold, the site of the reconstruction is scanned using computed tomography (CT). The 2D CT scan data is then converted to a 3D CAD file, which can then be rectified to achieve the desired scaffold shape. The rectified CAD model is further interpolated into a series of 2D layers using computer software, and then transferred to the rapid prototyping machine for processing the definitive scaffold. Scaffolds made by using RP technologies have a highly controlled and reproducible porosity, pore size and geometry, and well-defined 3D structures. In addition, this technology offers the ease and flexibility of varying the scaffold characteristics to meet specific structural and functional requirements of the tissue of interest

Filament Fabrication

(i) Polycaprolactone Filaments

Polycaprolactone (PCL) pellets can be obtained from Aldrich Chemical Company, Inc. (Milwaukee, Wis.) (Catalog No. 44,074-4). The semi-crystalline bioresorbable polymer has an average $M_n$ of ca. 80,000 (GPC) with a melt index of 1.0 g/10 min (125° C./44 psi ASTM D1238-73). It has a melting point of 60° C. (DSC) and a glass transition temperature of −60° C. The polymer pellets are kept in a dessicator prior to usage.

Filament fabrication is performed using a fiber-spinning machine (Alex James & Associates Inc., Greensville, S.C.). PCL pellets are melted at 190° C. in a cylinder by an external heating jacket. After a hold-time of 15 min, the temperature is lowered to 140° C. and the polymer melt is extruded through spinnerets with a die exit diameter of 0.064" (1.63 mm). Each batch of PCL pellets weighs 30±1 g. The piston speed is set at 10 mm/min. The extrudate is quenched in chilled water, placed 40 mm below the die exit. The combination of temperature, piston speed and height-drop to water quenching settings: produces a filament diameter of 1.70±0.10 mm. The PCL filaments are fabricated to have a consistent diameter to fit the drive wheels of an unmodified FDM system. The filaments are vacuum-dried and kept in a dessicator prior to usage.

(ii) Polycaprolactone/Hydroxyapatite (PCL/HA) Composite Filaments

Prior to usage, PCL pellets are dried at 4° C. for 24 hours in a vacuum oven. The PCL pellets are then added to an HA and methylene chloride mixture which is stirred on a platform shaker at 25° C. for 2 hours. The PCL/HA blend contains 25% content of HA. The polymer solution concentration used is 7% (w/w). The PCL/HA, composite foam is formed by casting the solvent mixture on a glass tray at 25° C. for 24 hours to evaporate the solvent. The composite foam is cut into square bits less than 0.5 cm×0.5 cm. The composite pellets are then stored in a dessicator until filament production.

Filament fabrication is carried out as described above for PCL filaments using a fiber-spinning machine. The polymer pellets are melted at 150° C. in a cylinder by an external heating jacket. After the set temperature is reached, a hold time of 15 min was followed before extruding the melt through a spinnerette with a die exit 0.064" (1.625 mm) in diameter. The extrudate is quenched in water placed 40 mm below the die exit. The piston speed is set at 1 cm/min. The combination of temperature, piston speed and height-drop to water quenching settings produces a filament diameter of 1.75±0.10mm and a length of 8.0±0.2 m.

Scaffold Fabrication

Scaffolds are fabricated using PCL or PCL/HA filaments with a FDM 3D Modeler rapid prototyping system from Stratasys Inc. (Eden Prairie, Minn.). Slices of the CAD model in .STL format are generated on Stratasys' QuickSlice (QS) software with a specified slice thickness. The amount and direction of the extrudate (called "raster" in FDM's context) are determined by configuring various build parameters for individual layers. The build parameters include the road width of rasters, fill gap between rasters, slice thickness and raster angle. Specific combinations of these parameters and the liquefier temperature are required to achieve smooth and consistent extrudate flow and raster deposition with sufficient adhesion between adjacent layers. The head speed, fill gap, and raster angle for every layer are programmed through the QS software and saved as an .SLC, the (Slice) file format. The 2D slice data is then converted into the QS.SML (Stratasys Machine Language) file format that automatically generates the build paths based on the input parameters for each slice layer. The FDM parameters for the processing of PCL and PCL/HA composite scaffolds are'set out in Table 1. Table 2 shows the effect of these parameters on the geometry of the scaffold structure. The .SML data is sent to the FDM machine to fabricate the scaffold, specimens. The liquefier temperature is set at 120° C. ±10° C. and the envelope temperature remains at 25±2° C. (ambient temperature) throughout the fabrication process.

To achieve consistent flow, the FDM machine has to be modified in respect to cooling of the entrance of the filament into the liquefier. In addition, cooling of the nozzle tip with air allows the machine to run with a higher flow rate. Hence, an optimized FDM process involves complex interactions among the hardware, software and material properties. The liquefier temperature and the filament feed rate has the most direct influence on the material flow for the fabrication of porous models.

TABLE 1

FDM Parameters For The Processing of PCL and PCL/HA Scaffolds

Software: Stratasys' QuickSlice (QS)
Material Dependent Values:
(workable range for PCL and PCL/HA filaments Ø1.8 ± 0.1 mm)

| | |
|---|---|
| Start Delay(s) | 0.16–0.18 |
| Start Flow(s) | 13–14 |
| Flow Rate (×10⁻ in/s) | 30–50 |
| Shutoff Distance (×10⁻³ in) | (−33)–(−29) |
| Rollback (×10⁻³ in) | 167–171 |
| Head Speed (×10⁻³ in/s) | 50–100 |
| Liquefier Temperature (° C.) | 120–140 |
| Slice Thickness (in) | 0.008–0.010 |
| Nozzle Size (in) | 0.010 and 0.016 |
| Lay-down Pattern (°) | 0/90 |
| | 0/60/120 |

TABLE 1-continued

FDM Parameters For The Processing of
PCL and PCL/HA Scaffolds

| | 0/72/144/36/108 |
|---|---|
| Scaffold Characteristics: | |
| (range of values obtained via various parameter combinations) | |
| Porosity (%) | 43–75 |
| Channel Width ($\mu$m) | 250–780 |
| Filament Thickness ($\mu$m) | 190–350 |

TABLE 2

Scaffold Characteristics Resulting From
Setting Different FDM Build Parameters

| FDM Build Parameters | Scaffold Characteristics |
|---|---|
| Road width of rasters | Wall thickness |
| Fill gap between rasters | Horizontal channel width |
| Slice thickness | Vertical channel width |
| Raster angle | Lay-down pattern |

To obtain a specific extrudate diameter for a constant volumetric flow, the minimum roller speed is determined by using a low FDM head speed (4–8 mm/s) for steady material deposition in a minimum fabrication time. The optimum values of liquefier temperature and filament feed rate are obtained through iterative modification to achieve a target raster road width.

The road width (RW) is targeted slightly above the inner diameter of the smallest nozzle tip in use, for stable flow during extrusion. With the smallest nozzle tip T10 (inner diameter 0.010 in), the target RW is set as approximately 0.254 mm. Thin layers of trial specimens with a slice thickness (ST) of 0.254 mm are fabricated in succession until the target RW is achieved. The workable range of FDM liquefier temperature and roller speed are determined as 125±10° C. and 0.080±0.01 rps respectively for processing the filaments. The next larger tip size T16 (0.016 in) can also be used without changing the build or flow parameters. A smaller nozzle size is used to fabricate similar wafers of finer internal structures.

Scaffolds of various porosities are produced by setting a constant ratio of the wall thickness to the channel width for every layer. Various lay-down patterns are possible, giving rise to complex 3D geometrical patterns. Preferred combinations of flow rate, head speed and liquefier temperature have been established to produce sufficient adhesion between extrudate of adjacent layers at their cross-points while maintaining vertical channels between them to provide interconnectivity throughout the entire scaffold structure.

The FDM process described above allows the design of 3D scaffolds in a multi-layer design within the same gross architectural structure. The structure of the scaffolds designed and fabricated using the FDM method is highly similar to the honeycomb of a bee, with its regular array of identical pores, when viewed in the z-direction of the fabrication process. The main difference lies in the shape of the pores: the bee's honeycomb comprises hexagonal pores surrounded by solid faces/walls which nest together to fill a plane, whereas the FDM scaffold structure is built from inter-crossing filaments stacked in horizontal planes and comprises pores surrounded by solid edges/struts.

Figure 2:
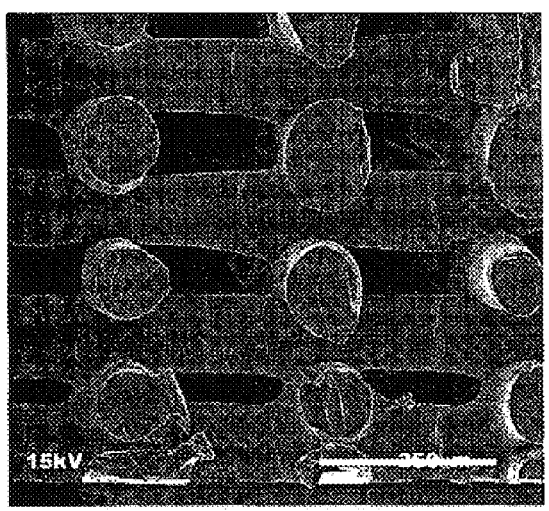
FIGS. 2A and 2B show the SEM pictures of the cross-sectional and top views of a PCL scaffold based on a 0/90° lay-down pattern fabricated using a 0.016" (0.41 mm) nozzle.
Figure 2:
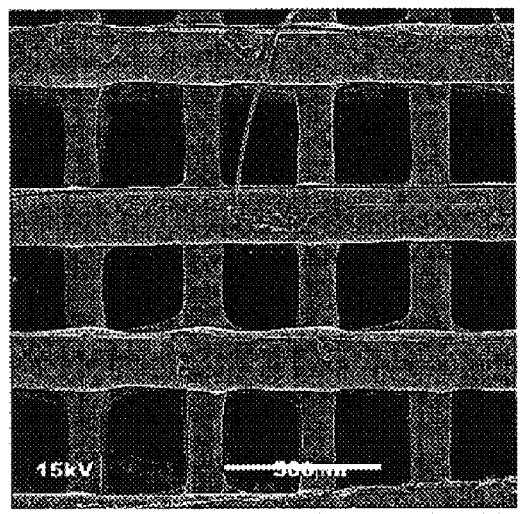
Figure 3:
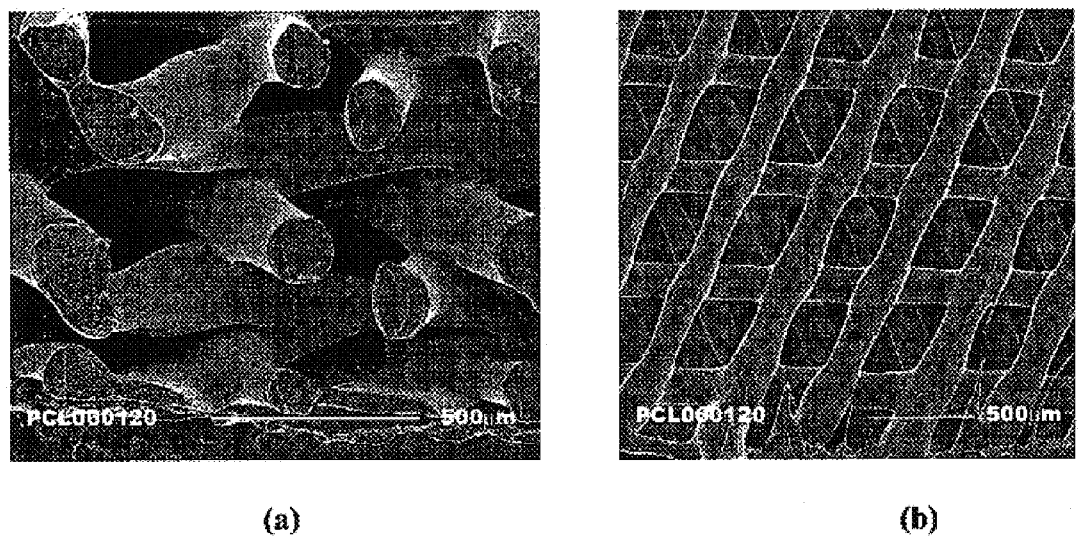
FIGS. 3A and 3B show the SEM pictures of the cross-sectional and top views of a PCL scaffold based on a 0/60/120° lay-down pattern.
Figure 4:
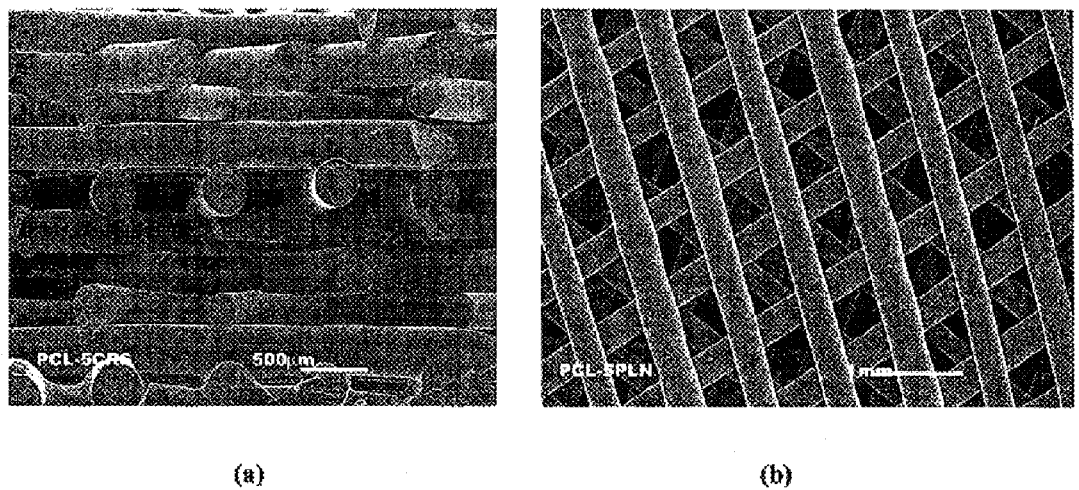
FIGS. 4A and 4B show the SEM pictures of the cross-sectional and top views of a PCL scaffold based on a 0/72/144/36/108° lay-down pattern.

The 0/90° lay-down pattern results in square pores. Lay-down patterns of 0/60/120° and 0/72/144/36/108° are used to give a honeycomb-like pattern of triangular and polygonal pores, respectively. The three lay-down patterns can be clearly observed using SEM as seen in FIGS. 2, 3 and 4. The size of the honeycomb pores is in the range 200–700 $\mu$m. The scaffold can also be made up of layers of different lay-down patterns. Despite being fabricated with different lay-down patterns, the porosity of the layers can be made identical. The porosity is controllable both by varying the channel size during the design process and also by modifying the flow conditions through the FDM head during processing.

The porosity of the scaffolds range from 30% to 80%, calculated from PCL's specific density of 1.145, and the measured mass and external dimensions of each wafer specimen. The scaffolds consist of deposited layers of bars/struts 260–370 $\mu$m in diameter. The interconnected pores and large internal surface areas of the bioresorbable scaffold structures make them suitable for tissue engineering applications. The scaffold designs also allow the flow transport of nutrients and wastes, and have the capacity to deliver a high volume of cells. The scaffolds have chemical and physical properties that allow load-bearing applications, as well as allowing active tissue integration of bone and cartilage tissue components and vascularization to enhance nutrient transport.

The scaffold has degradation and resorption kinetics of 6 to 12 months and the capacity to maintain a given space under biomechanical stress/loading for 6 months. Incorporation of a bioresorbable ceramic, for example tricalcium-phosphate or hydroxyapatite, in the bioresorbable, synthetic and natural polymer, produces a hybrid/composite material support triggering the desired degradation and resorption kinetics. Such a composite material improves the biocompatibility and hard tissue integration inasmuch as HA/TCP particles, which are embedded into the synthetic polymer matrix, allow for increased initial flash spread of serum proteins compared to the more hydrophobic polymer surface. The basic resorption products of the HA/TCP also help buffer the acidic resorption by-products of the aliphatic polyester and thereby help to avoid the formation of an unfavorable environment for the hard tissue cells due to a decreased pH.

The PCL scaffolds are suitable for use in tissue engineering applications, such as is described below.

Customization of PCL Scaffold to Individual Patient's Requirements

For clinical applications, the CT and/or MRI data of the individual patient is transformed into an STL file to process the custom made bioresorbable scaffolds.

Figure 5:
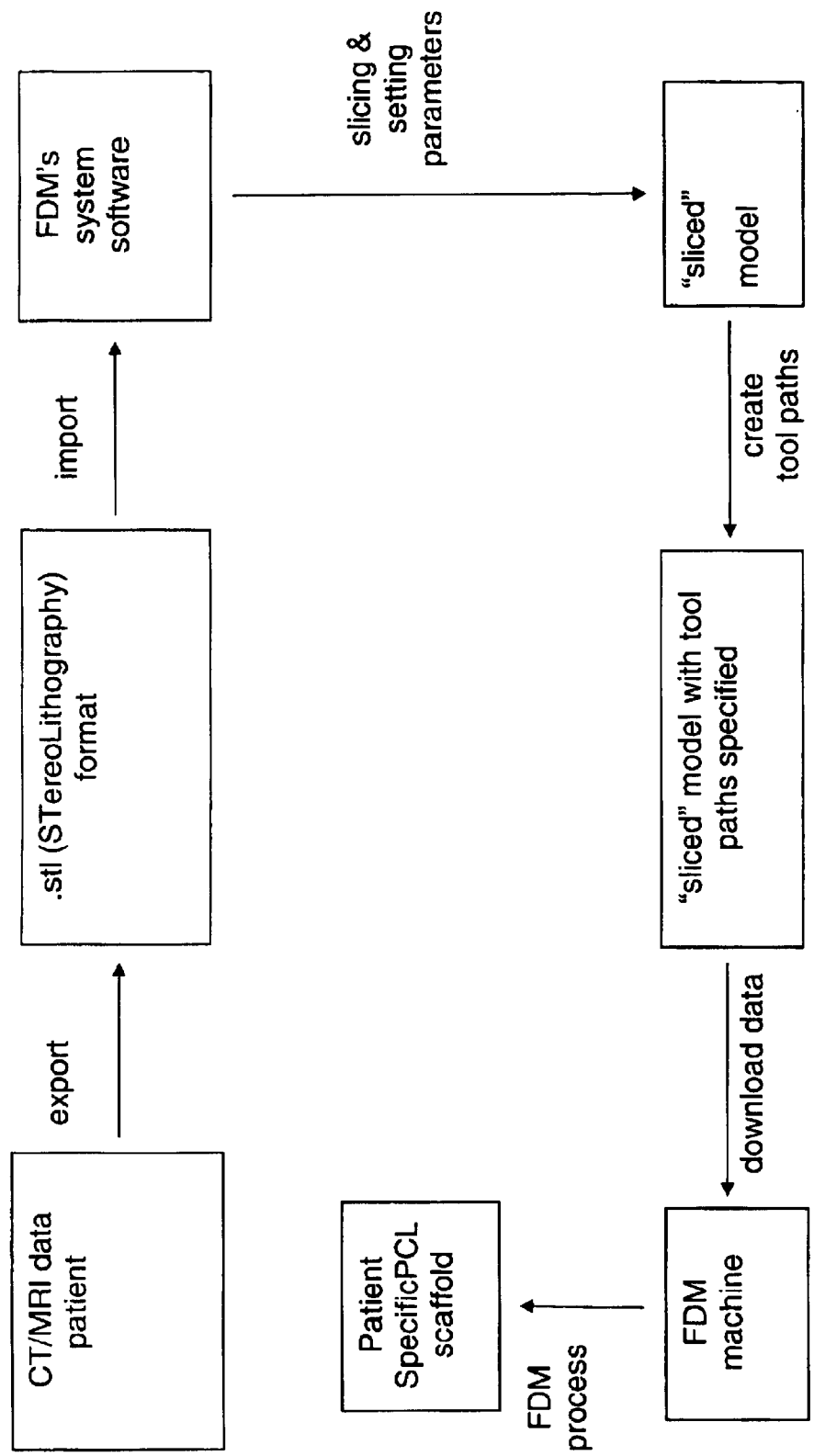
FIG. 5 represents a flow diagram of the process of fabricating a patient specific scaffold via the FMD process.

For example, digital scanning is used to digitize the surface topography of an anatomical model. The model is mounted on the platter within the set scan boundaries. The scanning process begins at the bottom of the model and proceeds upward section by section. At each section the laser translates horizontally left to right while the object is rotated on the platter. The measurement accuracy is ±0.001 inch and the rotational resolution is 0.004 degrees. The acquired data is then verified, minimally edited, triangulated and sectioned to obtain only the desired zone before exporting the file in STL data format to the FDM QuickSlice software for setting the road patterns of the individual layers prior to the actual building of the physical part. A flow diagram of the process is depicted in FIG. 5.

Tissue-engineered Osteochondral Transplant

Figure 7:
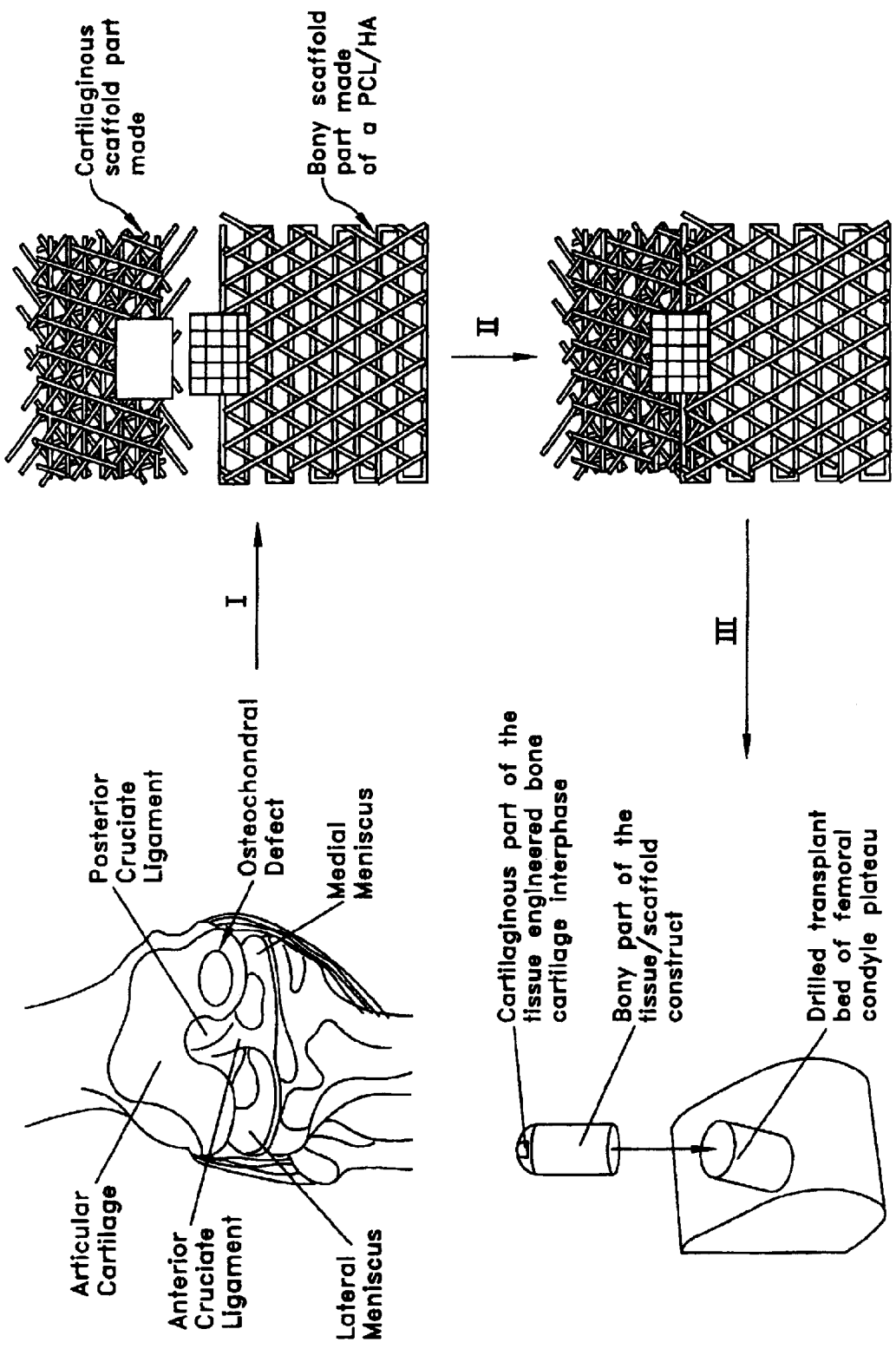
FIG. 7 is a schematic illustration of the culture concept and the surgical placement of a tissue-engineered osteochondral transplant. (I) after the loading of the bony scaffold part with osteoblasts and cartilage scaffolds with chondrocytes, the constructs are cultured for 28 days in osteogenic and cartilaginous culture media, respectively; (II) after separate culturing, the bony and cartilage scaffolds are joined together and further cultured for 4 weeks in a 50/50% mixture of the osteogenic and chondrogenic media; and (III) the dental cylinder implantlike design of the bony bioresorbable 3D scaffold allows applying a press fit; hence, a secure and user-friendly transplantation is obtained

FIG. 7 is a schematic illustration of the culture concept and the surgical placement of a tissue-engineered osteochondral transplant. After the loading of the PCL scaffold part with osteoblasts and cartilage scaffolds with chondrocytes, the constructs are cultured for 28 days in osteogenic and cartilaginous culture media respectively. After separate culturing, the bony and cartilage scaffolds are joined together and further cultured for 4 weeks in a 50/50% mixture of the osteogenic and chondrogenic media. The dental cylinder implant-like design of the bony bioresorbable 3D scaffold allows applying a press fit. Hence, a secure and user-friendly transplantation is obtained.

Bone Tissue Engineering

For load-bearing tissues such as cartilage and: bone, any bioresorbable 3D scaffold should provide sufficient mechanical strength over a certain period of time to withstand in vitro and/or in vivo forces. The space for cell proliferation and differentiation, extracellular matrix production, and finally tissue growth and remodeling, has to be maintained until the tissue inside the scaffold architecture is mature enough to support itself. The PCL scaffold is design ed to retain its mechanical properties for 5 to 6 months and then gradually lose its physical properties until it is completely metabolized over a period of two years. The compression stiffness of PCL scaffolds ranged from 4 to 77 MPa when tested in air and is therefore comparable to human trabecular bone. There is a decrease in compressive stiffness and yield strength when the PCT scaffolds are tested under simulated physiological conditions when compared to ambient conditions. The decrease was less significant for PCL scaffolds manufactured by FDM than what has reported by other groups, which used foam-like scaffolds made of copolymers of PGA and PLA for bone tissue engineering.

In vivo, the ratio between actively proliferating bone surface area and the maximum depth penetration inside an osteoblast-seeded scaffold is based on the fact that bone formation is subject to a delicate metabolic balance. Hence, in order for a "living" tissue engineered bone graft (as well as any other type of bone graft) to succeed, it is essential that vascularisation be facilitated. Particularly in large scaffolds, the central areas inside the matrix might be the last to become vascularized after a long lasting time of ischemia with unfavorable metabolic conditions for mineralized bone formation. The completely interconnected and highly regular honeycomb-like pore morphology, as well as the large channel interconnections of the PCL scaffolds independent from the lay-down pattern, supports the development of a vascular network, which is able to regulate the transport of nutrients and waste in the entire scaffold architecture, In contrast, it is known that foam-like scaffolds with small pore interconnections do not provide a morphology that favors bone formation and vascularization.

Cartilage Tissue Engineering

The PCT scaffold is seeded with chondrocytes in combination with a collagen-based hydrogel and embedded in a fibrin glue capsule to protect the transplants from an immunological reaction from the host tissue. The scaffold/cell constructs are then cultured before implantation.

The mechanical properties of the PCL scaffold enables it to withstand the contraction forces of the hematoma during wound healing, which protects and allows the hydrogel to stay in place after implantation. Chondrocytes are thus able to proliferate and produce ECM within a physiological-like environment. The risk of transplant reabsorption and/or shrinkage, which results in unsatisfactory functional and aesthetic failure, may be avoided.

Bone Grafting in Craniofacial Surgery

The computer tomography (CT) and/or magnetic resonance imaging (MRI) data of an individual patient's craniofacial defect is converted into an .STL file to fabricate the custom made bioresorbable 3D scaffolds. The operating time is reduced with the preoperative modeled bone grafts. Those custom made implants minimize the trial and error associated with shaping of graft materials during surgery.

EXAMPLE 1

(i) Scaffold Fabrication

Scaffold specimens were fabricated using PCL and PCL/HA filaments as described above with a FDM 3D Modeler rapid prototyping system from Stratasys Inc. (Eden Prairie, Minn.). Blocks of 32.0 (length×25.5 (width)×13.5 mm (height) with a 61% porosity were created directly in the Stratasys' QuickSlice (QS) software. The head speed, fill gap, and raster angle for every layer were programmed through the QS software and saved as an .SLC, the (Slice) file format. Lay-down patterns of 0/60/120° and 0/72/144/36/108° were used to give a honeycomb-like pattern of triangular and polygonal pores, respectively.

The 2D slice data were converted into QS's .SML (Stratasys Machine Language) file format that automatically generated the build paths based on the input parameters for each slice layer. The .SML data was sent to the FDM machine to fabricate the scaffold specimens using a T16 tip. The liquefier temperature was set at 120° C. and the envelope temperature remained at 25 2° C. (ambient temperature) throughout the fabrication process. After manufacture, the four specimens of each configuration were cut with an ultra sharp blade into slightly smaller blocks with dimensions 28.0 (length)×21.0 (width)×13.5 mm (height). One each of these new blocks was used to measure the porosity of the design and then all four specimens were each divided into twelve small scaffold specimens (6.5×6.5×13.5 mm) for microscopically characterization and compression testing, as described in the following sections.

(ii) Porosity Calculation

The ratio of the apparent volume to the true volume of the scaffolds was used to calculate the porosity of each design configuration. An ultrapycnometer (Quantachrome Ultrapycnometer 1000, Quantachrome Corporation, Boynton Beach, Fla.) was used to measure the volume of the PCL scaffolds (6.5×6.5×13.5 mm) at 25° C. in pure argon; three measurements were made on each specimen and the mean was used in the porosity calculations. For cellular solids with pore sizes bigger then 100 $\mu$m, ultrapycnometer porosimetry tends to underestimate the true porosity. Therefore, the porosity was also calculated by the following method: (I) measuring the weight and volume of each sample; (II) calculating from these measurements the apparent density of the PCL scaffolds p*=m (g)/V (cm$^3$); and (III) using the formula:

$$\text{porosity} = \epsilon = 1 - \rho^*/\rho \times 100\% \, (\rho_{PCL} = 1{,}145 \text{ g/cm}^3)$$

(iii) Microscopic Characterization

One each of the scaffold specimens measuring 6.5×6.5×13.5 mm was used to measure the pore size and morphology of the scaffold on scanning electron microscopy (SEM) photographs. The specimens were freeze-fractured after dipping in liquid nitrogen for 30 min. Fracture surfaces were then gold sputtered using a JEOL fine coater JFC-1200 at 10 mA for 12 s. These were studied using a JEOL scanning electron microscope JSM-5800LV operating at 15 kV.

(iv) Mechanical Testing

In order to determine the effect of the physiological environment on the compressive properties of PCL scaffolds, scaffolds were tested under the following two conditions: (1) a in phosphate buffered saline solution (PBS) preconditioned in PBS for 1 day; or (2) at ambient conditions. Six samples (6.5×6.5×13.5 mm) of each design configuration were tested on an Instron 4502 Uniaxial Testing System and a 1-kN load-cell (Canton, Mass.) following the guidelines set in ASTM F451-99a Standard Specification for Acrylic Bone Cement. The specimens were compressed at a rate of 1 mm/min up to a strain-level of approximately 0.7 mm/mm. Young's modulus (MPa) was calculated, from the stress-strain curve, as the slope of the initial linear portion of the curve, neglecting any toe region due to initial settling of the specimen. Compressive strength at yield was defined as the intersection of the stress-strain curve with the modulus slope at an offset of 1.0% strain. For the mechanical properties measured, a Student's t-test was performed in comparing means from two independent sample groups. A significance level of 0.05 was used in all the statistical tests performed. MiniTab statistics software version 12.2 (MiniTab Inc., State College, Pa.) was used for statistical analysis.

(v) Results

Porosity Calculation and Microscopical Characterization. Ultrapycnometer measurements revealed a porosity of 55% and 56% for PCL scaffolds with lay-down patterns of 0/60/120° (FIG. 3) and 0/72/144/36/108° (FIG. 4), respectively. In comparison, porosimetry calculation via the apparent density resulted in a 61%±1 for both scaffold architectures. The pore morphology measured, based on SEM micrographs, fell within the range of 380×430×590 µm and 360×410×620 µm, respectively.

Compression Testing. Statistical analysis of the results was used to compare the stiffness and the compressive 1% offset yield strength. A Student's t-test for independent variables was used to check for differences between results obtained from the two different designs, after normality, which is a prerequisite for using the t-test, had been established using an Andersen-Darling test. The scaffolds with a 0/60/120° lay-down pattern had compressive stiffness and 1% offset yield strength in air of 41.9±3.5 MPa and 3.1±0.1 MPa respectively, and in simulated physiological conditions (saline solution at 37° C.) 29.4±4.0 MPa and 2.3±0.2 MPa, respectively. In comparison, the scaffolds with a 0/72/144/36/108° lay-down pattern had compressive stiffness and I% offset yield strength in air of 41.9±3.5 MPa and 3.1±0.1 MPa respectively, and in simulated physiological conditions (saline solution at 37° C.) 29.4±4.0 MPa and 2.3±0.2 MPa, respectively. Statistical analysis confirmed that the 5 angle scaffolds had significantly lower stiffness and 1% offset yield strengths under compression loading than those with a 3 angle pattern under both testing conditions ($p \leq 0.05$).

EXAMPLE 2

(i) Cell Culture Experiments

One day prior to cell seeding, the 3D scaffolds were sterilized in 70% ethanol overnight. The ethanol was removed by centrifuging three times in changes of phosphate buffered saline (PBS) for 15 minutes with 1000 rpm.

(ii) Fibroblast Cultures and Seeding

Human fibroblasts were harvested from the Anterior Cruciate Ligament (ACL) of a 34 year old male patient. The fibroblasts were isolated via enzyme digestion by incubating at 37° C., 5% $CO_2$ for 12 hrs with a collagenase-trypsin solution (Sigma, St Louis, Mo.). After the fourth passage, cultures were trypsinized and cell viability was examined via trypan blue (Sigma, St Louis, Mo.) exclusion. The cell pellets obtained after centrifuging the trypsinized cell suspensions8were resuspended in 300 µl of DMEM and 450,000 cells in 30 µl were carefully seeded onto 16 scaffolds with a micropipette. The seeded scaffolds were left untouched for 2 hours to allow for protein secretion and cell attachment. A 2 ml culture medium was then added to each well, so that the scaffolds were fully submerged. The specimens were then placed for four weeks in a self-sterilizable incubator (WTB Binder, Tuttlingen, Germany) at 37° C. in 5% $CO_2$, 95% air, and 99% relative humidity.

(iii) Osteoprogenitor Cell Cultures and Seeding

Primary human osteoprogenitor cells were isolated under sterile conditions by stripping periosteum from the skull of a patient who underwent craniofacial surgery. Monolayer cell culture flasks were filled with 3 to 5 small pieces and Dulbecos Modified Eagle medium (Gibco, Grand Island N.Y., USA) with 10% fetal bovine serum, 1% penicillin, and 1% streptomycin and 1% amphoterecin. In addition, 50.0 mgL ascorbic acid was added to promote the osteoblastic phenotype. Then the flasks were placed in a self-sterilizable incubator (WTB Binder, Tuttlingen, Germany) at 37° C. in 5% $CO_2$, 95% air, and 99% relative humidity. After the monolayer-culture grew to confluence and exhibited nodule formation, the osteoblast-like cells were harvested using a 0.05% trypsinethylendiamine tetra-acetic acid (EDTA) solution, split, resuspended in culture medium and filled into new culture flasks. The culture media was replaced every third or fourth day. Alkaline phosphatase and osteocalcin staining verified the osteoblastic-phenotype. After confluent monolayers were achieved by the fourth passage, the cells were enzymatically lifted from the flask using 0.25% Trypsin/EDTA (Hyclone Utah, USA) and counted using a hemocytometer. The cell mortality was less than 5% as shown by trypan blue staining and maintained a stable cell metabolism. Cell pellets were resuspended and aliquots of 15 µml containing 50,000 cells were seeded onto the top of PCL scaffolds measuring 6×6×2 mm. Subsequently, the seeded scaffolds were placed into an incubator to allow the cells to build adhesion plaques on the polymer surface. After 2 hours, 1 ml of complete media was added into each well. Cell-scaffold constructs were then cultured for a period of 3 weeks.

(iv) Phase Contrast Light and Scanning Electron Microscopy

The establishment of the fibroblast and osteoblast-like phenotype, intercellular connections, and extracellular matrix production were examined daily by phase-contrast light microscopy for three and four weeks, respectively. Adhesion of the cells and their distribution was studied via environmental scanning electron microscopy (ESEM). Specimens were fixed in 2.5% gluteraldehyde (Merck, Germany) for at least 4 hrs at 4° C. They were then dehydrated in a graded ethanol series of 30%, 50%, 90% and 100% for 5 mins at each grade, dried, and examined with a Jeol JSM-5800LV SEM at 15 kV.

(v) Confocal Laser Microscopy and Immunohistochemistry

Cell/scaffold constructs were prepared for confocal laser microscopy (CLM) by staining viable cells green with the fluorescent dye Fluorescein Diacetate (FDA, Molecular Probes Inc., Oregon). The 3D cultures were incubated at 37° C. with 2 μg/ml FDA in PBS for 15 minutes. After rinsing twice in PBS, each sample was then placed in 1 mg/ml Propidium Iodide solution (PI, Molecular Probes, Oregon) for 2 mins at room temperature to stain dead cells red. The samples were then rinsed twice in PBS and viewed under a Confocal Laser Microscope (Olympus IX70-HLSH100. Fluoview). Depth projection images were constructed from up to 25 horizontal image sections through the cultures.

Samples were first fixed in 3.7% formaldehyde, at room temperature, for 30 mins. After rinsing 2 times with PBS at 5 mins each time, 200 μg/ml RNAse A was added and left for 30 mins at room temperature. Phalloidin (A12379 Alexa Fluo 488 phalloidin, Molecular Probes Inc., Oregon) was then added at in a 1:200 dilution for 45 mins at room temperature and in darkness. Samples were subsequently counterstained with 5 μg/ml Propidium Iodide solution, dried and mounted for viewing under fluorescence microscope.

(vi) Results

Fibroblast Seeding and Culture. The cells started attaching onto PCL scaffold surfaces 2 hours postseeding. The cells that adhered to the PCL matrix initially were spherical in shape. After two to three days in culture, the fibroblasts migrated and developed an interconnecting network of cells. In the first culturing week the cells used the rods and struts as templates for their proliferation and a multilayered cell lawn could be detected in the SEM. By day eight, fibroblasts were seen throughout the entire scaffold with a strong presence of extracellular matrix. On week two, the fibroblast started to bridge the walls of the fully interconnected pore network via three-dimensional extracellular matrix production. From this time point, the cell-to-cell contact points and the extracellular matrix and culture media acted as a template. In general, the cells started the 3D growth process at the junctions of the bars and struts. By this phenomenon, the cells were able to three-dimensionally bridge distances of up to 10 times the size of a cell. After the cells had grown over the entire surfaces of the rods and struts, they started filling up the pores in a circular manner. In week 4 the complete 3D scaffold architecture was taken up by cell/tissue formation.

These results show that human fibroblasts colonize on the struts and bars of an FDM fabricated. PCL scaffold can form a cell to cell and cell to extracellular matrix, interconnective network throughout the entire 3D honeycomb-like architecture. In the entire PCL 3D scaffold architecture, the formation of actin supported sheet-like protrusions known as lamellipodia occurs up to a period of three weeks.

Seeding and Culture of Osteoblast-Like Cells. Osteoblast-like cells started attaching by focal contacts 2 hours post-seeding. Cells actively colonized the surface of the PCL matrix after only 4 days in culture. Osteoblast-like cells showed a three-dimensional phenotype and established their tentacle-like enlargements of the plasma membrane known as filipodia. In the first 3 to 5 days, cells were arranged in a swirling pattern, and individual cells had a long, thin, spindle-shaped morphology. Microscopically, it was observed that the cells had attached and spread on the PCL bars and cross sections presenting a star-shaped morphology. At the interconnected pores, the cells appeared to grow along the rods and span across the pore architecture. Over the 3-week period, a centripetal cell ingrowth within the pores could be observed, with the extracellular matrix acting as a guiding structure for the cells. Phallodin staining and SEM revealed a net-like growth structure. On the basis of these described qualitative data, a significant difference of the proliferation patterns of the two different scaffold architectures could not be observed. In another study, a quantitative comparison of cell attachment and proliferation on the surface of PCL scaffolds with six different matrix architectures a cell proliferation assay was performed. The data reveal that scaffolds with a 0/60/120° lay-down pattern have a higher proliferation rate in the first two weeks whereas scaffolds with a 0/72/144/36/108° lay-down overtake the three-angle matrix architecture in week three and four.

The PCL/osteoblasts constructs were implanted in the nude mice model for bone tissue engineering in vivo studies. The histological and immunothistochemical analysis of the explanted PCL scaffoldd-tissue constructs showed that vascularized and mineralized bone-like tissue can be generated in a nude mice model by using the PCL scaffolds.

EXAMPLE 3

(i) Seeding and Culture of Chondrocytes

A study was performed to evaluate three scaffold/cell constructs with different physical and chemical properties, in their potential for tissue engineering elastic cartilage. Group I consisted of PCL scaffolds; Group II, custom-made non-woven PGA fibers; and Group III, collagen sponges. Chondrocytes were isolated from an ear cartilage biopsy of 2 year old male piglets and seeded in combination with a collagen based hydrogel and embedded in a fibrin glue capsule to protect the transplants from an immunological reaction from the host tissue. The specimens; were then cultured for 1 week. The scaffold/cell constructs and controls were placed subcutaneously on the paravertebral fascia for 4½ month.

From the analysis of the histological, immunohistochemical, mechanical, and physico-chemical results of the tissue inside the different scaffolds, it was concluded that a PCL matrix supports cartilage formation whereas a textile construct made of PGA and a bovine collagen type I foam allowed only the formation of fibrous and calcified tissue. Chondrocytes were embedded in a fibrin glue/collagen gel matrix which was intended to act as a cell carrier and an immune barrier. Although such a hydrogel capsule itself causes an immunological host response, angiogenesis comparison of the three investigated scaffold groups showed that the PCL group showed a slightly increased fibrocytic reaction at the outside of the explants whereas the group II and III specimens showed highly vascularized fibrous tissue formation.

In vitro engineered PCL scaffold-tissue constructs were, studied for their ability to generate elastic cartilage in an immunocompetent animal model. From the Analysis of the histological, immunohistochemical, mechanical, and physico-chemical results of the tissue inside the scaffolds, it can be concluded that a PCL matrix supports cartilage formation whereas a textile construct made of PGA and a bovine collagen type I foam allowed only the formation of fibrous and calcified tissue.

EXAMPLE 4

(i) Custom Made Bioresorbable Scaffolds

Figure 6:
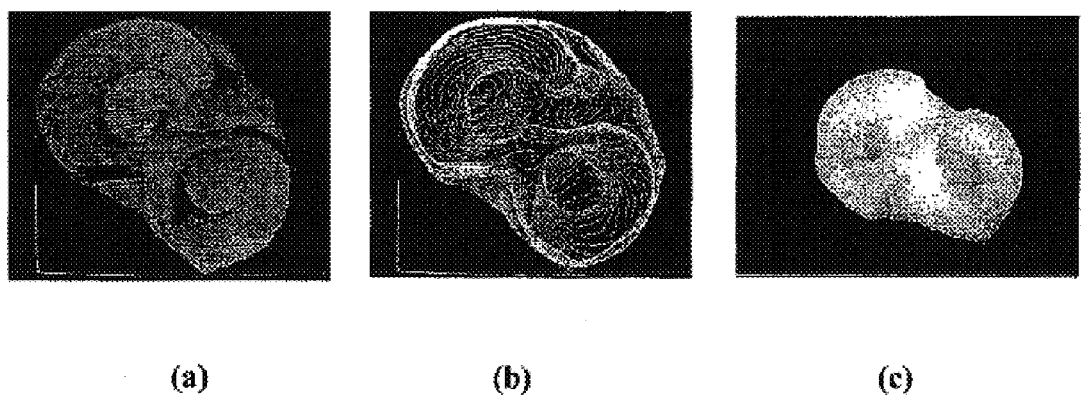
FIGS. 6A, 6B, and 6C show the sectioned portion of the tibia/meniscus zone.

A Digibot II 3D Laser Digitizing System (Digibotics Inc., Austin, Tex.) was used to digitize the surface topography of an anatomical model of the proximal human femoral bone with attached meniscus. The model was mounted on the platter within the set scan boundaries. The scanning process began at the bottom of the model and proceeded upward section by section. At each section the laser translated horizontally left to right while the object rotated on the platter. The measurement accuracy was ±0.001 inch and the rotational resolution was 0.004 degrees. The acquired data was verified, minimally edited, triangulated and sectioned to obtain only the tibia/meniscus zone before exporting the file in STL data format to the FDM QuickSlice software for setting the road patterns of individual layers priori to the actual building of the physical part. FIGS. 6A, 6B, and 6C show the sectioned portion of the tibia/meniscus zone.

What is claimed is:

1. A method for fabricating a filament for use in tissue engineering, said method comprising:
   providing a polycaprolactone material;
   melting said polycaprolactone material at a first given temperature to form a polycaprolactone melt;
   holding the temperature of said polycaprolactone melt at said first given temperature for a given amount of time;
   lowering the temperature of said polycaprolactone melt from said first given temperature to a second given temperature after the step of holding the temperature of said polycaprolactone melt at said first given temperature for said given amount of time;
   extruding said polycaprolactone melt through a fiber-spinning machine, said fiber-spinning machine having spinnerets with a die exit of a given diameter, a piston set at a given speed, and a vertical drop of a given distance from said die exit to a cooling material positioned below said die exit, wherein the combination of said second given temperature, said given die exit diameter, said given piston speed, and said given distance of said vertical drop produces said filament with a given diameter for use in tissue engineering.

2. A method for fabricating a filament for use in tissue engineering according to claim 1 wherein said given diameter of said filament corresponds to drive wheels of an unmodified Fused Deposition Modeling (FDM) system.

3. A method for fabricating a filament for use in tissue engineering according to claim 2 wherein said filament is configured to have a constant diameter.

4. A method for fabricating a filament for use in tissue engineering according to claim 1 wherein said filament is vacuum-dried prior to usage.

5. A method for fabricating a filament for use in tissue engineering according to claim 1 wherein said filament is kept in a dessicator prior to usage.

6. A method for fabricating a filament for use in tissue engineering according to claim 1 wherein said filament is vacuum-dried and kept in a dessicator prior to usage.

7. A method for fabricating a filament for use in tissue engineering according to claim 1 wherein said polycaprolactone material as initially provided is in the form of pellets.

8. A method for fabricating a filament for use in tissue engineering according to claim 1 wherein said first given temperature is about 190° C.

9. A method for fabricating a filament for use in tissue engineering according to claim 1 wherein said given amount of time is about 15 minutes.

10. A method for fabricating a filament for use in tissue engineering according to claim 1 wherein said second given temperature is about 140° C.

11. A method for fabricating a filament for use in tissue engineering according to claim 1 wherein said given diameter of said die exit is about 1.63 mm.

12. A method for fabricating a filament for use in tissue engineering according to claim 1 wherein said given speed of said piston is set at about 10 mm/min.

13. A method for fabricating a filament for use in tissue engineering according to claim 1 wherein said given distance of said vertical drop from said die exit to said cooling material is about 40 mm.

14. A method for fabricating a filament for use in tissue engineering according to claim 1 wherein said cooling material is water.

15. A method for fabricating a filament for use in tissue engineering according to claim 1 wherein said given diameter of said filament includes a range of about 1.60 mm to about 1.80 mm.

16. A method for fabricating a filament for use in tissue engineering according to claim 1 wherein said given diameter of said filament is about 1.70 mm.

17. A method for fabricating a filament for use in tissue engineering, said method of fabricating said filament comprising:
   providing polycaprolactone pellets;
   melting said polycaprolactone pellets at about 190° C. to form a polycaprolactone melt;
   holding the temperature of said polycaprolactone melt at about 190° C. for about 15 minutes;
   lowering the temperature of said polycaprolactone melt from said first given temperature to about 140° C. after the step of holding the temperature of said polycaprolactone melt at about 190° C. for about 15 minutes; and
   extruding said polycaprolactone melt through a fiber-spinning machine, said fiber-spinning machine having spinnerets with a die exit of about 1.63 mm, a piston set at about 10 mm/min, and a vertical drop of about 40 mm from said die exit to water positioned below said die exit, wherein the combination of said lower temperature of about 140° C., said die exit diameter of about 1.63, said piston speed of about 10 mm/min, and said vertical drop of about 40 mm produces said filament with a given diameter for use in tissue engineering;
   wherein said given diameter of said filament corresponds to drive wheels of an unmodified Fused Deposition Modeling (FDM) system;
   wherein said filament is configured to have a constant diameter; and
   wherein said filament is vacuum-dried and kept in a dessicator prior to usage.

18. A method for fabricating a filament for use in tissue engineering, said method comprising:
   providing a polycaprolactone material;
   drying said polycaprolactone material at a first given temperature for a first given amount of time to form a dried polycaprolactone material;
   combining said dried polycaprolactone material with a HA and methylene chloride mixture to form a PCL/HA blend;
   stirring said PCL/HA blend at a second given temperature for a second given amount of time to form a solvent mixture;
   casting said solvent mixture on a tray at a third given temperature for a third given amount of time to evaporate said solvent mixture to form a PCL/HA composite foam material;
   melting said PCL/HA composite foam material at a fourth given temperature to form a PCL/HA melt;

holding the temperature of said PCL/HA melt at said fourth given temperature for a fourth given amount of time;

lowering the temperature of said PCL/HA melt from said fourth given temperature to a fifth given temperature after the step of holding the temperature of said PCL/HA melt at said fourth given temperature for said fourth given amount of time; and extruding said PCL/HA melt through a fiber-spinning machine, said fiber spinning machine having spinnerets with a die exit of a given diameter, a piston set at a given speed, and a vertical drop of a given distance from said die exit to a cooling material positioned below said die exit, wherein the combination of said fifth given temperature, said given die exit diameter, said given piston speed, and said given distance of said vertical drop produces said filament with a given diameter for use in tissue engineering.

19. A method for fabricating a filament for use in tissue engineering according to claim 18 wherein said first given temperature during the step of drying said polycaprolactone material is about 40° C.

20. A method for fabricating a filament for use in tissue engineering according to claim 18 wherein said first given amount of time for drying said polycaprolactone is about 24 hours.

21. A method for fabricating a filament for use in tissue engineering according to claim 18 wherein the step of drying said polycaprolactone material is in a vacuum oven.

22. A method for fabricating a filament for use in tissue engineering according to claim 18 wherein said second given temperature during the step of stirring said PCL/HA blend is about 25° C.

23. A method for fabricating a filament for use in tissue engineering according to claim 18 wherein said second given amount of time during the step of stirring said PCL/HA blend is about 2 hours.

24. A method for fabricating a filament for use in tissue engineering according to claim 18 wherein the step of stirring said PCL/HA blend is on a platform shaker.

25. A method for fabricating a filament for use in tissue engineering according to claim 18 wherein said third given temperature during the step of casting said solvent on said tray is about 25° C.

26. A method for fabricating a filament for use in tissue engineering according to claim 18 wherein said third given amount of time during the step of casting said solvent on said tray is about 24 hours.

27. A method for fabricating a filament for use in tissue engineering according to claim 18 wherein said tray is formed of glass.

28. A method for fabricating a filament for use in tissue engineering according to claim 18 wherein said fourth given temperature during the step of melting said PCL/HA composite foam material is about 150° C.

29. A method for fabricating a filament for use in tissue engineering according to claim 18 wherein said fourth given amount of time during the step of holding the temperature of said PCL/HA melt at said fourth given temperature is about 15 minutes.

30. A method for fabricating a filament for use in tissue engineering according to claim 18 wherein said given diameter of said die exit is about 1.625 mm.

31. A method for fabricating a filament for use in tissue engineering according to claim 18 wherein said given speed of said piston is set at about 1 cm/min.

32. A method for fabricating a filament for use in tissue engineering according to claim 18 wherein said given distance of said vertical drop from said die exit to said cooling material is about 40 mm.

33. A method for fabricating a filament for use in tissue engineering according to claim 18 wherein said cooling material is water.

34. A method for fabricating a filament for use in tissue engineering according to claim 18 wherein said given diameter of said filament includes a range of about 1.65 mm to about 1.85 mm.

35. A method for fabricating a filament for use in tissue engineering according to claim 18 wherein said given diameter of said filament is about 1.75 mm.

36. A method for fabricating a filament for use in tissue engineering according to claim 18 wherein said filament has a length in the range of about 7.8 m to about 8.2 m.

37. A method for fabricating a filament for use in tissue engineering according to claim 18 wherein said filament has a length of about 8.0 m.

38. A method for fabricating a filament for use in tissue engineering according to claim 18 further comprising the step of storing said PCL/HA composite foam material in a dessicator prior to the step of melting said PCL/HA composite foam material so as to form said filament.

39. A method for fabricating a filament for use in tissue engineering according to claim 18 wherein said PCL/HA blend has a 25% content of HA.

* * * * *